May 12, 1942. R. L. BYRUM Plant Pat. 515
ROSE PLANT
Filed Oct. 3, 1941
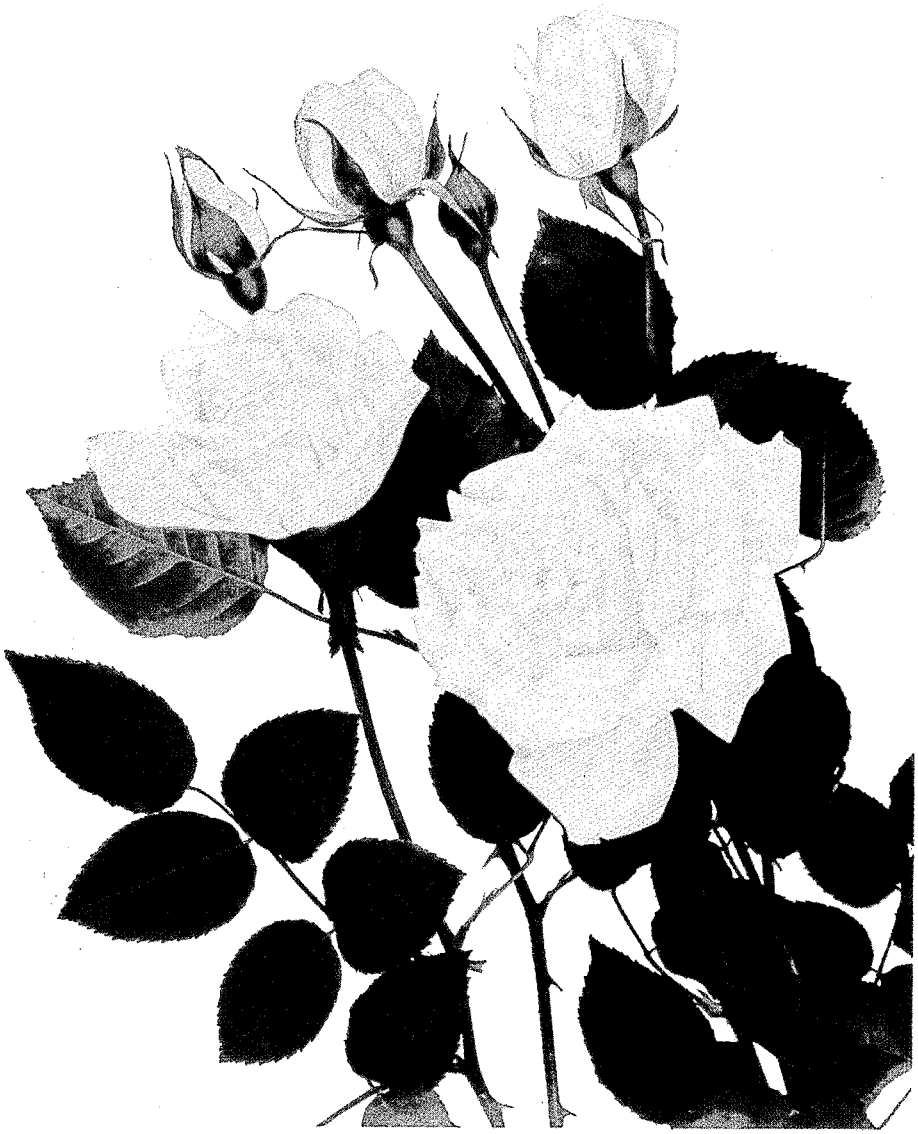
Inventor
Roy L. Byrum
By Robb & Robb
Attorneys Patented May 12, 1942

UNITED STATES PATENT OFFICE

515

ROSE PLANT

Roy L. Byrum, Richmond, Ind., assignor to Joseph H. Hill Company, Richmond, Ind., a corporation of Indiana Application October 3, 1941, Serial No. 413,553

1 Claim. (Cl. 47—61)

The present invention relates to a new and distinct variety of hybrid tea rose plant, originating as a seedling from crossing the two well known varieties "Joanna Hill" and "R. M. S. Queen Mary" (Plant Patent No. 249).

This new rose possesses characteristics found in neither of its parents, or other roses of the same type. In form it is most similar to its pollen parent, but it is distinguished from either, primarily, by the difference in color of its flowers, its greater productivity and larger blooms, and it is exceptionally good for both summer and winter forcing.

These characteristics, as well as other important ones, are set forth in the following detail description of the new rose, color terminology being in accord with Ridgway's Color Standard:

Type: Bush; green house; seedling; for cut flowers.
Class: Hybrid Tea.
Breeding or discovery: Seedling.
*Seed parent.*—"Joanna Hill."
*Pollen parent.*—"R. M. S. Queen Mary."
Propagation: Holds its distinguishing characteristics through succeeding propagations by cutting, grafting and budding.

*Flower*

Locality where grown: Richmond, Indiana.
Flowers borne: Singly on strong, long stems.
Quantity of bloom: Abundant in greenhouse.
Continuity: Continuous.
Fragrance: Slight; tea.
Bud:
*Peduncle.*—Medium length; heavy; erect; Parrot Green, Plate VI; almost smooth; few prickles.
*Before calyx breaks.*—*Size*—large. *Form*—short, pointed with a conspicuous neck; with foliaceous appendages on the surface of the bud; with much cut foliaceous parts extending beyond the tip of the bud equal to three-fourths or more of its length.
*As calyx breaks.*—*Color*—when first showing, Jasper Red, Plate XIII, and Apricot Buff, Plate XIV. *As opens more*—Jasper Red, Plate XIII, and Apricot Buff, Plate XIV, with spot of Clear Dull Green-Yellow, Plate XVII, at base of petal.
*As first petal opens.*—*Size*—very large. *Form*—short; globular. *Color*—outside—around outer edge, Old Rose, Plate XIII; balance Apricot Buff, Plate XIV, with Light Viridine Yellow, Plate V. Inside—mainly flesh pink, Plate XIII, with Primuline Yellow, Plate XVI, toward base of petal. *Opening*—opens up well.

Bloom:
*Size.*—When fully open, very large; five inches to six inches.
*Petalage.*—Very double; from fifty to sixty petals arranged irregularly.
*Form.*—Very full; globular at first; becoming open; petals at first remaining loosely rolled outward, becoming later, at maturity, loosely rolled outward.
Petals: Thick, with inside and outside satiny.
*Shape*—Outside—obovate, with apex flat with no notches. Intermediate—obovate, with apex flat with no notches. Inside—obovate, with apex flat with one notch.

This description of a newly opened flower was made from a rose grown in a greenhouse in the month of July, 1941, at Richmond, Indiana:

*Color.*—Outside petal: outside surface—outer edges are Venetian Pink, Plate XIII, to Citron Yellow toward base, Plate XVI. Inside surface—Flesh Pink, Plate XIII, to Amber Yellow base, Plate XVI. Intermediate petal: outside surface—outer edges are Venetian Pink, Plate XIII, to Citron Yellow toward base, Plate XVI. Inside surface—Flesh Pink, Plate XIII, to Amber Yellow base, Plate XVI. Inner petal: outside surface—Alizarine Pink, Plate XIII; Amber Yellow base. Inside surface.—Venetian Pink, Plate XIII; Amber Yellow base.

This description was made from a rose that was open for three days in a greenhouse in the month of September, 1941, at Richmond, Indiana:

*Color.*—Outside petal: outside surface—White overlaid with pale Cinnamon-Pink, Plate XXIX; Amber Yellow base, Plate XVI. Inside surface—White; Amber Yellow base, Plate XVI. Inside petal: outside surface—Pale Congo Pink, Plate XXVIII; Amber Yellow base, Plate XVI. Inside surface—Pale Cinnamon Pink, Plate XXIX; Amber Yellow base, Plate XVI.
*General color effect.*—Newly opened flower—Venetian Pink, Plate XIII. Three days open—Pale Congo Pink, Plate XXVIII.
*Behavior.*—Persist.
*Flower longevity.*—Cut roses grown in greenhouse kept at living room temperatures four to five days in August.

*Reproductive organs*

Stamens: Many arranged irregularly about pistils; mixed with petaloids.
Filaments: Medium length; reddish; most with anthers.

Anthers: Medium size; yellow; all open at various times.
Pollen: Very abundant; Gold.
Pistils: Very many.
Styles: Very uneven; medium length; medium heavy; bunched.
Stigma: White.
Ovaries: Some protruding from calyx.
Hips: Ovoid with inconspicuous neck; Yellow; very smooth; walls thick, fleshy.
Sepals: Permanent; moderately long; curled.
*Color.*—Inside—Light Cress Green, Plate XXXI, overlaid with white fuzz. Outside—Cress Green, Plate XXXI.
Seeds: Many; medium size.

*Plant*

Foliage:
*Leaves.*—Five to seven; abundant; very large; heavy; leathery.
*Leaflets.*—Ovoid, with apex acute; base obtuse; margin simply serrate.
*Color.*—*Mature*—upper surface—Dull Dark Yellow Green, Plate XXXII. Under surface—Deep Dull Yellow Green, #1, Plate XXXII. *Young* — upper surface — Light Green. Under surface—Bronze.
*Rachis (the supporting stem of the compound leaf).*—Heavy; under side sparsely hairy.
*Stipules.*—Medium length; moderately narrow; with moderately long points, turning out at an angle of less than 45°.
*Disease.*—Resistant to mildew and blackspot.

Growth:
*Habit.*—Bush; upright; much branched.
*Growth.*—Vigorous.
*Canes.*—Heavy.
*Main stems.*—Dull Green. *Thorns*—several; medium length; hooked downward; with narrow base. *Prickles* — none. *Hairs* — none.
*Branches.*—Bright Green. *Thorns*—several; medium length; hooked downward; with short, narrow base. *Prickles*—none. *Hairs*—none.
*New shoots.*—Dull Bronze. *Thorns*—several; medium length; hooked downward; with short, narrow base. *Prickles*—none. *Hairs*—none.

I claim:

A new and distinct variety of Hybrid Tea rose plant, characterized as to novelty by its great productivity, by the delicate color combination, large size and number of petals of the flowers, and its exceptional value for both summer and winter forcing, substantially as shown and described.

ROY L. BYRUM.